(12) United States Patent
Szymczak et al.

(10) Patent No.: US 7,691,409 B2
(45) Date of Patent: *Apr. 6, 2010

(54) SIMETHICONE SOLID ORAL DOSAGE FORM

(75) Inventors: Christopher E. Szymczak, Marlton, NJ (US); James T. Walter, Ambler, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 676 days.

This patent is subject to a terminal disclaimer.

(21) Appl. No.: 11/460,741

(22) Filed: Jul. 28, 2006

(65) Prior Publication Data

US 2007/0196468 A1 Aug. 23, 2007

Related U.S. Application Data

(62) Division of application No. 09/966,441, filed on Sep. 28, 2001, now Pat. No. 7,101,573.

(51) Int. Cl.
  *A61K 31/12* (2006.01)
  *A61K 33/12* (2006.01)
  *A61K 31/15* (2006.01)
  *A61K 31/165* (2006.01)
  *A61K 31/445* (2006.01)

(52) U.S. Cl. .................. 424/464; 424/489; 514/63

(58) Field of Classification Search .................. None
  See application file for complete search history.

(56) References Cited

U.S. PATENT DOCUMENTS

| 4,744,987 | A | 5/1988 | Mehra et al. |
| 4,851,226 | A | 7/1989 | Julian et al. |
| 4,906,478 | A | 3/1990 | Valentine et al. |
| 5,073,384 | A | 12/1991 | Valentine et al. |
| 5,075,114 | A | 12/1991 | Roche |
| 5,248,505 | A | 9/1993 | Garwin |
| 5,275,822 | A | 1/1994 | Valentine et al. |
| 5,458,886 | A | 10/1995 | Briquet |
| 5,489,436 | A | 2/1996 | Hoy et al. |
| 5,599,557 | A | 2/1997 | Johnson et al. |
| 5,679,376 | A | 10/1997 | Stevens et al. |
| 5,817,340 | A | 10/1998 | Roche et al. |
| 6,103,260 | A | 8/2000 | Luber et al. |
| 6,106,865 | A | 8/2000 | Staniforth et al. |
| 6,190,696 | B1 | 2/2001 | Groenewoud |

FOREIGN PATENT DOCUMENTS

| EP | 0659403 A2 | 6/1995 |
| JP | 398241 | 5/1964 |
| JP | 5097681 A2 | 4/1993 |
| WO | WO 95/11671 A1 | 5/1995 |
| WO | WO 9511671 A1 * | 5/1995 |
| WO | WO 00/13678 A1 | 3/2000 |

OTHER PUBLICATIONS

Lachman et al.: "The Theory and Practice of Industrial Pharmacy"; Chapter 11, 3$^{rd}$ Ed., pp. 293-345.
Lieberman et al.: "Pharmaceutical Dosage Forms", Tablets, vol. 2., 2$^{nd}$ Ed., Marcel Dekker Inc. 1990, p. 213-217 and 327-329.
Tobyn et al.: "Physicochemical comparison between microcrystalline cellulose and silicified microcrystalline cellulose", Int. J. Pharm. 168, 183-194.
Database CA 'Online! Chemical Abstracts Service, Kissei Pharmaceutical Co., Ltd., Japan: "Adsorbents for tableting oily materials" retrieved from STN Database accession No. 96:187285 HCA XP002225224.
Database WPI Section Ch. Week 200136 Derwent Publications Ltd., London, GB; AN 1993-164356 XP002225225.

* cited by examiner

*Primary Examiner*—Brian-Yong S Kwon

(57) ABSTRACT

The present invention provides a composition for forming a compressed solid dosage form that is a free-flowing compressible admixture of simethicone, an adsorbant, and an optional active agent, wherein the weight ratio of simethicone to adsorbent is at least 1:2.22. Also included are solid dosage forms made from a free-flowing compressible admixture of simethicone, an adsorbant, and an optional active agent, wherein the weight ratio of simethicone to adsorbent is at least 1:2.22.

20 Claims, No Drawings

SIMETHICONE SOLID ORAL DOSAGE FORM

CROSS REFERENCE TO RELATED APPLICATIONS

This application is a divisional of pending U.S. patent application Ser. No. 09/966,441, filed Sep. 28, 2001 now U.S. Pat. No. 7,101,573, currently pending. The Complete disclosure of the aforementioned related United States patent application and patent is hereby incorporated herein by reference for all purposes.

FIELD OF THE INVENTION

The present invention is directed to a free-flowing compressible composition containing simethicone and an adsorbent for forming a solid dosage form, such solid oral dosage forms and related processes.

BACKGROUND OF THE INVENTION

Active agents, e.g., pharmaceuticals, nutraceuticals, and the like, intended for oral administration are often provided in solid form as tablets, capsules, pills, lozenges, or granules. Oral dosage forms are swallowed whole, chewed in the mouth, disintegrated in the mouth and swallowed, or dissolved sublingually.

When administered orally, simethicone is used as an adjunct in the symptomatic treatment of flatulence, functional gastric bloating, and postoperative gas pains. The clinical use of simethicone is based on its antifoam properties. Silicone antifoams spread on the surface of aqueous liquids, forming a film of low surface tension and thus causing the collapse of foam bubbles. Thus, for self medication in over-the-counter preparations, simethicone is used as an antiflatulent to relieve symptoms commonly referred to as gas, including upper GI bloating, pressure, fullness, or stuffed feeling. It is often combined with other gastrointestinal medications, such as antacids, antispasmodics or digestive enzymes and various simethicone formulations are previously disclosed.

Simethicone can be administered orally as a liquid preparation or as solid form for example capsules, chewable or swallowable tablets. The advantage of tablets over liquids is the ease of portability. The advantages of swallowable tablets over chewable tablets include the ease of ingestion and lack of taste. Coated tablets are preferred for swallowable tablets.

Historically, in preparing solid simethicone dosage forms, difficulties have been encountered when attempting to incorporate substantial quantities of the liquid simethicone in the solid final blend for tableting. The difficulty has been to achieve sufficient flowability for processing and sufficient cohesion for compaction, particularly for direct compression tableting, so that the tablet will withstand the rigors of further processing, e.g., film coating, gelatin dipping, printing, packaging and the like. Likewise, difficulties have been encountered in assuring that the viscous liquid simethicone is uniformly distributed throughout the solid formulation and expeditiously dispersed upon administration.

Japanese Patent No. SHO 39[1961]-46451 to Kitsusho Yakuhin Kogyo KK discloses a method for preparing simethicone tablets by mixing and granulating simethicone with aluminium silicate, magnesium aluminum metasilicate, and magnesium silicate. In particular, the formulation disclosed by the above Japanese patent requires at most 25% simethicone and 75% or greater silicate, binder and dispersing agent. Binders were disclosed as being starch and lactose. Dispersing agent was disclosed as being carboxymethylcellulose. Further, the above Japanese patent discloses that when the amount of simethicone exceeds 25%, a portion of the simethicone can be carried away, therefore the tablet workability is not desirable.

JP 5097681 to Horii Yakuhin Kogyo KK discloses a preparation wherein simethicone is adsorbed to magnesium aluminate metasilicate and dextrin. Excipient was then added and the preparation was tableted. Following tableting a hydroxypropyl methylcellulose phthalate coating was added, followed by applying additional simethicone and gelatin. The amount of simethicone in the final tablet was about 15%.

U.S. Pat. No. 4,906,478 discloses a simethicone preparation including a powdered combinate of particulate calcium silicate and simethicone. U.S. Pat. No. 5,073,384 discloses simethicone preparations including combinates of water soluble agglomerated maltodextrin and simethicone. U.S. Pat. No. 5,458,886 discloses a free-flowing granular composition including titanium dioxide having specific particle size and surface area in combination with simethicone.

U.S. Pat. No. 6,103,260 describes the use of an admixture of simethicone and either one or both of granular anhydrous tribasic calcium phosphate or dibasic calcium, wherein the admixture in a uniform granular composition of not more than 1000 micron particle size, that is suitable for compression into a solid dosage form for oral administration. While the amount of simethicone in the final composition was disclosed as being 10% to 50%, the final tablet weight was in excess of 1000 mg.

What is needed, therefore, is a free-flowing compressible composition containing simethicone for forming a solid dosage, wherein either larger quantities of simethicone can be incorporated therein or smaller solid dosage forms containing the same amount of simethicone.

Surprisingly, it has been discovered that using silicified microcrystalline cellulose and magnesium aluminometasilicate as substrates onto which simethicone or other oil or liquid active is adsorbed provides such a composition. Thus, there is provided by the present invention a free-flowing compressible composition containing simethicone for forming a solid dosage form that contains either larger weight percentages of simethicone while maintaining substantially the same size than previously possible or the same weight percentage of simethicone in a smaller size. In addition, the present invention is directed to such solid oral dosage forms and related processes.

SUMMARY OF THE INVENTION

The present invention provides a composition for forming a compressed solid dosage form that is a free-flowing compressible admixture of simethicone, an adsorbant, and an optional active agent, wherein the weight ratio of simethicone to adsorbent is at least 1:2.22. Also included are solid dosage forms made from a free-flowing compressible admixture of simethicone, an adsorbant, and an optional active agent, wherein the weight ratio of simethicone to adsorbent is at least 1:2.22.

DETAILED DESCRIPTION OF THE INVENTION

The term, "active agent" is used herein in a broad sense and encompasses any material that can be carried by or entrained in the system. For example, the active agent can be a pharmaceutical, nutraceutical, vitamin, dietary supplement, nutrient, or the like and combinations thereof.

The active agents useful herein can be selected from classes from those in the following therapeutic categories: ace-inhibitors; alkaloids; antacids; analgesics; anabolic agents; anti-anginal drugs; anti-allergy agents; anti-arrhythmia agents; antiasthmatics; antibiotics; anticholesterolemics; anticonvulsants; anticoagulants; antidepressants; antidiarrheal preparations; anti-emetics; antihistamines; antihypertensives; anti-infectives; anti-inflammatories; antilipid agents; antimanics; anti-migraine agents; antinauseants; antipsychotics; antistroke agents; antithyroid preparations; anabolic drugs; antiobesity agents; antiparasitics; antipsychotics; antipyretics; antispasmodics; antithrombotics; antitumor agents; antitussives; antiulcer agents; anti-uricemia agents; anxiolytic agents; appetite stimulants; appetite suppressants; beta-blocking agents; bronchodilators; cardiovascular agents; cerebral dilators; chelating agents; cholecystokinin antagonists and agonists; chemotherapeutic agents; cognition activators; contraceptives; coronary dilators; cough suppressants; decongestants; deodorants; dermatological agents; diabetes agents; diuretics; emollients; enzymes; erythropoietic drugs; expectorants; fertility agents; fungicides; gastrointestinal agents; growth regulators; hormone replacement agents; hyperglycemic agents; hypoglycemic agents; ion-exchange resins; laxatives; migraine treatments; mineral supplements; mucolytics, narcotics; neuroleptics; neuromuscular drugs; non-steroidal anti-inflammatories (NSAIDs); nutritional additives; peripheral vasodilators; polypeptides; prostaglandins; psychotropics; renin inhibitors; respiratory stimulants; sedatives; steroids; stimulants; sympatholytics; thyroid preparations; tranquilizers; uterine relaxants; vaginal preparations; vasoconstrictors; vasodilators; vertigo agents; vitamins; wound healing agents; and others.

Active agents that may be used in the invention include, but are not limited to: acetaminophen; acetic acid; acetylsalicylic acid, including its buffered forms; acrivastine; albuterol and its sulfate; alcohol; alkaline phosphatase; allantoin; aloe; aluminum acetate, carbonate, chloral hydrate; alprazolam; amino acids; aminobenzoic acid; amoxicillin; ampicillin; amsacrine; amsalog; anethole; ascorbic acid; aspartame; astemizole; atenolol; azatadine and its maleate; bacitracin; balsam peru; beclomethasone dipropionate; benzocaine; benzoic acid; benzophenones; benzoyl peroxide; benzquinamide and its hydrochloride; bethanechol; biotin; bisacodyl; bismuth subsalicylate; bornyl acetate; brompheniramine and its maleate; buspirone; caffeine; calamine; calcium carbonate, caseinate and hydroxide; camphor; captopril; carmustine; cascara sagrada; castor oil; cefaclor; cefadroxil; cephalexin; centrizine and its hydrochloride; cetirizine; cetyl alcohol; cetylpyridinium chloride; chelated minerals; chloramphenicol; chlorcyclizine hydrochloride; chlorhexidine gluconate; chloroxylenol; chloropentostatin; chlorpheniramine and its maleate and tannate salts; chlorpromazine; cholestyramine resin; choline bitartrate; chondrogenic stimulating protein; cimetidine; cinnamedrine hydrochloride; citalopram; citric acid; clarithromycin; clemastine and its fumarate; clonidine; clofibrate; cocoa butter; cod liver oil; codeine and its fumarate and phosphate; cortisone acetate; ciprofloxacin HCl; cyanocobalamin; cyclizine hydrochloride; cyproheptadine; danthron; dexbrompheniramine maleate; dextromethorphan and its hydrohalides; diazepam; dibucaine; dichloralphenazone; diclofenac sodium; digoxin; dihydroergotamine and its hydrogenates/mesylates; diltiazem; dimethicone; dioxybenzone; diphenhydramine and its citrate salt; diphenhydramine and its hydrochloride; divalproex and its alkali metal salts; docusate calcium, potassium, and sodium; doxycycline hydrate; doxylamine succinate; dronabinol; efaroxan; enalapril; enoxacin; ergotamine and its tartrate; erythromycin; estropipate; ethinyl estradiol; ephedrine; epinephrine bitartrate; erythropoietin; eucalyptol; famotidine; fenoprofen and its metal salts; ferrous fumarate, gluconate and sulfate; fexofenadine; fluoxetine; folic acid; fosphenytoin; 5-fluorouracil (5-FU); fluoxetine; flurbiprofen; furosemide; gabapentin; gentamicin; gemfibrozil; glipizide; glycerin; glyceryl stearate; granisetron; griseofulvin; growth hormone; guaifenesin; hexylresorcinol; hydrochlorothiazide; hydrocodone and its tartrates; hydrocortisone and its acetate; 8-hydroxyquinoline sulfate; hydroxyzine and its pamoate and hydrochloride salts; ibuprofen; indomethacin; inositol; insulin; iodine; ipecac; iron; isosorbide and its mono- and di-nitrates; isoxicam; ketamine; kaolin; ketoprofen; lactic acid; lactase, lanolin; lecithin; leuprolide acetate; lidocaine and its hydrochloride salt; lisinopril; liotrix; loperamide, loratadine; lovastatin; luteinizing hormone; LHRH (luteinizing hormone replacement hormone); magnesium carbonate, hydroxide, salicylate, and trisilicate; meclizine; mefenamic acid; meclofenamic acid; meclofenamate sodium; medroxyprogesterone acetate; methenamine mandelate; menthol; meperidine hydrochloride; metaproterenol sulfate; methscopolamine and its nitrates; methysergide and its maleate; methyl nicotinate; methyl salicylate; methyl cellulose; methsuximide; metoclopramide and its halides/hydrates; metronidazole; metoprol tartrate; miconazole nitrate; mineral oil; minoxidil; morphine; naproxen and its alkali metal sodium salts; nifedipine; neomycin sulfate; niacin; niacinamide; nicotine; nicotinamide; nimesulide; nitroglycerin; nonoxynol-9; norethindrone and its acetate; nystatin; octoxynol; octoxynol-9; octyl dimethyl PABA; octyl methoxycinnamate; olsalazine; omega-3 polyunsaturated fatty acids; omeprazole; ondansetron and its hydrochloride; oxolinic acid; oxybenzone; oxtriphylline; para-aminobenzoic acid (PABA); padimate-O; paramethadione; pentostatin; peppermint oil; pentaerythritol tetranitrate; pentobarbital sodium; perphenazine; phenelzine sulfate; phenindamine and its tartrate; pheniramine maleate; phenobarbital; phenol; phenolphthalein; phenylephrine and its tannates and hydrochlorides; phenylpropanolamine; phenytoin; pirmenol; piroxicam and its salts; polydimethylsiloxanes; polymixin B sulfate; potassium chloride and nitrate; prazepam; procainamide hydrochloride; procaterol; promethazine and its hydrochloride; propoxyphene and its hydrochloride and napsylate; pramiracetam; pramoxine and its hydrochloride salt; prochlorperazine and its maleate; propranolol and its hydrochloride; promethazine and its hydrochloride; propranolol; pseudoephedrine and its sulfates and hydrochlorides; pyridoxine; pyrilamine and its hydrochlorides and tannates; quinapril; quinidine gluconate and sulfate; quinestrol; ranitidine; resorcinol; riboflavin; salicylic acid; scopolamine; sesame oil; shark liver oil; simethicone; sodium bicarbonate, citrate, and fluoride; sucralfate; sulfamethoxazole; sulfasalazine; sulfur; sumatriptan and its succinate; tacrine and its hydrochloride; theophylline; terfenadine; thiethylperazine and its maleate; timolol and its maleate; tioperidone; tramadol; trimetrexate; triazolam; tretinoin; tetracycline hydrochloride; tolmetin; tolnaftate; triclosan; trimethobenzamide and its hydrochloride; tripelennamine and its hydrochloride; triprolidine hydrochloride; undecylenic acid; vancomycin; verapamil hydrochloride; vidarabine phosphate; vitamins and minerals; witch hazel; xylometazoline hydrochloride; zinc; zinc sulfate; zinc undecylenate. Active agents may further include, but are not limited to food acids; insoluble metal and mineral hydroxides, carbonates, oxides, polycarbophils, and salts thereof; adsorbates of active drugs on a magnesium trisilicate base and on a magnesium aluminum silicate base, and mixtures thereof. Mixtures and pharmaceutically acceptable salts of these and other actives can be used.

Examples of suitable active agents include stimulent laxatives, such as bisacodyl, cascara sagrada, danthron, senna, phenolphthalein, aloe, castor oil, ricinoleic acid, and dehydrocholic acid, and mixtures thereof; antisecretory; H2 receptor antagonists, such as famotadine, which is commercially available from McNeil-PPC, Inc. under the PEPCID brand; proton pump inhibitors; gastrointestinal cytoprotectives, such as sucraflate and misoprostol; gastrointestinal prokinetics, such as Prucalopride, antibiotics for *H. pylori*, such as clarithromycin, amoxicillin, tetracycline, and metronidazole; antidiarrheals, such as diphenoxylate and loperamide, which is commercially available from McNeil-PPC, Inc. under the IMMODIUM brand; glycopyrrolate, such as Robinul; antiemetics, such as Ondansetron, analgesics, such as mesalamine, commerically available under the ASACOL brand, aspirin, and salicylic acid; and mixtures thereof.

In one embodiment, the additional active agent may be selected from bisacodyl, famotadine, prucalopride, diphenoxylate, loperamide, lactase, mesalamine, bismuth, and pharmaceutically acceptable salts, esters, isomers, and mixtures therof.

In another embodiment, the additional active agent may be selected from acetaminophen, ibuprofen, naproxen, ketoprofen, cyclobenzaprine, meloxicam, rofecoxib, celecoxib, and pharmaceutically acceptable salts, esters, isomers, and mixtures thereof.

Examples of suitable polydimethylsiloxanes, which include, but are not limited to dimethicone and simethicone, are those disclosed in U.S. Pat. No. 4,906,478, U.S. Pat. No. 5,275,822, and U.S. Pat. No. 6,103,260, the contents of each is expressly incorporated herein by reference. As used herein, the term simethicone refers to the broader class of polydimethylsiloxanes, including simethicone and dimethicone.

Suitable lactase for use herein include, a lactase isolated from *Saccharomyces lactis*, by Gist-Brocade in Delft, Holland, and sold by Enzyme Development Corporation, New York, N.Y.; a lactase from *Aspergillus oryzae*, Lactase Y-400, produced by K. K. Yakult Honsha; a lactase from *Aspergillus oryzae*, Plexazym LA 1, produced by Roehm GmbH; a lactase from *Aspergillus oryzae*, produced by Shinnihon Kagaku Kogyo Co.; a lactase from *Kluyveromyces fragilis*, produced by Sturges Enzymes, Selby, North Yorkshire, England; a lactase from *Aspergillus oryzae*, Takamine lactase, produced by Miles Laboratories, Inc., Elkhart, Ind.; a lactase from *Kluyveromyces fragilis* produced by Novo Enzymes, Bagsvaerd, Denmark, and a lactase from *Aspergillus oryzae*, e.g., Lactase F "Amano" 100, produced by Amano Pharmaceutical Co., Ltd. Naka-ku, Nagoya, Japan. These suppliers and others offer, generally, lactase composition, including a diluent, having a potency of between 14,000 and 100,000 FCC lactase units/gram.

The active agent can be in the form of a fine powder, granule, or large crystal, and has an average particle size from about 1 µm to about 1000 µm, also from about 150 µm to about 500 µm. Typically, the active agent used in the present invention has an average size of greater than 50 µm.

If the active agent has an objectionable taste, it may be coated with a taste masking coating, as known in the art. Examples of suitable taste masking coatings are described in U.S. Pat. No. 4,851,226, U.S. Pat. No. 5,075,114, and U.S. Pat. No. 5,489,436. Commercially available taste masked active agents may also be employed. For example, acetaminophen particles that are encapsulated with ethylcellulose or other polymers by a coaccervation process may be used in the present invention. Coaccervation-encapsulated acetaminophen may be purchased commercially from Eurand America, Inc. Vandalia, Ohio, or from Circa Inc., Dayton, Ohio.

As used herein, all ranges provided are intended to expressly include at least all numbers that fall between the endpoints of ranges.

As used herein, simethicone conforms to the United States Pharmacopoeia (USP XXII) definition, that is a mixture of fully methylated linear siloxane polymers containing repeating units of polydimethylsiloxane stabilized with trimethylsiloxy end-blocking units, and silicon dioxide. Also, as used herein, dimethicone can be substituted for simethcone. Simethicone contains about 90.5-99% of polydimethylsiloxane and about 4-7% silicon dioxide. The polydimethylsiloxanes present in simethicone are practically inert polymers having a molecular weight of 14,000-21,000. The mixture is a gray, translucent, viscous fluid that is insoluble in water.

Conventional excipients useful in the present include fillers or dry binders, such as water soluble simple and complex carbohydrate (e.g., sucrose, glucose, fructose, maltose, lactose, maltodextrins, starch, modified starches, mannitol, sorbitol, maltitol, xylitol, and erthritol), cellulose, and cellulosic derivatives (e.g., microcrystalline cellulose, carboxymethyl cellulose, and hydroxyethyl cellulose); wet binders, such as polyvinyl pyrrolidone, methycellulose, hydroxypropyl cellulose, hydroxypropyl methylcellulose, carboxymethylcellulose, xanthan gum, carrageenan gum, locust bean gum, alginates, and acacia; disintegrants, such as sodium starch glycolate, crosspovidone, crosscarmellose, microcrystalline cellulose, starch, and the like, lubricants, such as magnesium stearate, stearic acid and its pharmaceutically acceptable salts, talc, vegetable oils, and waxes; glidants, such as colloidal silicon dioxide; sweeteners, including aspartame, acesulfame potassium, sucralose and saccharin; flavors, acidulants, antioxidants, preservatives, surfactants, wetting agents, and coloring agents, and mixtures thereof.

As used herein, the term "adsorbant" means a solid material or combination of solid materials that is capable of adsorbing and carrying an oily or fluid material, such as simethicone, while retaining sufficient flowability to assure content uniformity and sufficient compactability to be processed into tablets using direct compression methods.

As used in the present invention, silicified microcrystalline cellulose may be the PROSOLV brand (PenWest Pharmaceuticals, Patterson, N.Y.).

As used herein magnesium aluminometasilicate may be the NEUSILIN brand, e.g., S1, FH2, US2, and UFL2 (Fuji Chemical Industries (USA) Inc., Robbinsville, N.J.).

In accordance with one embodiment of the present invention, simethicone is admixed with the magnesium aluminometasilicate to form a uniform free flowing granular admixture. The silicified microcrystalline cellulose is then added, as well as any optional additional active agent, and any additional excipients. The composition is then mixed until uniform. The resulting granular composition is then compressed.

In embodiments wherein one or more additional active agents are included, the additional active agent may optionally be admixed with the simethicone prior to adsorbing onto the magnesium aluminometasilicate and silicified microcrystalline cellulose. The resulting blend is then further blended with any additional active agents and any additional excipients, and compressed into tablets.

Generally, it is desired that the composition contains a proportionate amount of simethicone, magnesium aluminometasilicate, and silicified microcrystalline cellulose, which is consistent with forming a free-flowing granular composition. For example, the proportionate amounts, by weight, of the ingredients of the granular admixture composition is about 1: about 0.5 to about 0.85:about 0.9 to about 1.30 per solid dosage unit (simethicone:magnesium aluminometasilicate:silicified microcrystalline cellulose).

The weight ratio of simethicone to total adsorbant (e.g. magnesium aluminometasilicate and silicified microcrystalline cellulose) is at least about 1:2.22, for example at least about 1:2.00, or at least about 1:1.80. In one embodiment, the weight ratio of simethicone to total adsorbant is at least about 1 part simethicone to 1.75 parts adsorbant.

The solid dosage forms of the present invention may be shaped, in other words, formed, by a variety of methods known in the art. Optionally, the dosage form of the present invention, either with or without active agent, can be molded, deposited or compacted under methods commonly known in the art.

Solid dosage forms of the present invention may be formed by direct compression. Using this technique, the solid dosage forms are produced by directly compacting a blend of the active agent and any other appropriate inactive ingredients, i.e., excipients (e.g. flavoring, binders, lubricants, etc.). Any conventional compacting methods for forming a chewable dosage form may be used to make the soft core of the present invention. These methods include, but are not limited to, dry granulation followed by compression, and wet granulation followed by drying and compression. Compression methods include rotary compression, compacting roller technology, such as a chilsonator or drop roller, or by molding, casting, or extrusion technologies. These methods are well known in the art, and are described in detail in, for example, Lachman, et al., *The Theory and Practice of Industrial Pharmacy*, Chapter 11, (3$^{rd}$ Ed. 1986).

One such method utilizes placing a pre-determined volume of particles or components into a die cavity of a rotary tablet press, which continuously rotates as part of a die table from the filling position to a compaction position. At the compaction position, the particles are compacted between an upper punch and a lower punch. The die table then rotates to an ejection position, at which the resulting tablet is pushed from the die cavity by the lower punch and guided to an ejection chute by a stationary take-off bar.

On aspect of the present invention is a compressed solid dosage form, e.g., a tablet or a caplet. The hardness of the solid dosage form is up to about 20 kiloponds per square centimeter (kp/cm$^2$), e.g., about 2 to 15 kp/cm$^2$ or about 4 to 10 kp/cm$^2$. As used herein, the term hardness is used to describe the diametral breaking strength as measured by conventional pharmaceutical hardness testing equipment, such as a Schleuniger Hardness Tester. In order to compare values across different size tablets, the breaking strength is normalized for the area of the break (which may be approximated as tablet diameter times thickness). This normalized value, expressed in kp/cm$^2$, is sometimes referred in the art as tablet tensile strength. A general discussion of tablet hardness testing is found in Leiberman et al., *Pharmaceutical Dosage Forms—Tablets*, Volume 2, 2$^{nd}$ ed., Marcel Dekker Inc., 1990, pp. 213-217, 327-329.

The solid oral dosage forms of the present invention may be prepared in the form of tablets, caplets, gelcaps, capsules, chewable tablets, lozenges, fast dissolving wafers, and other known and effective solid oral delivery modes.

A typical solid dosage form of the present invention may contain a formulation containing various components in accordance with the following:

| | |
|---|---|
| Simethicone | about 1 to about 75% |
| Silicified microcrystalline cellulose | about 5 to about 40% |
| Magnesium aluminometasilicate | about 5 to about 30% |
| Additional Active agent | about 0 to about 89% |
| Lubricant | about 0 to about 5% |
| Filler/dry binder | about 0 to about 35% |
| Wet Binder | about 0 to about 10% |
| Flavorants/Colorants/Sweeteners | about 0 to about 5% |

All % are w/w %.

All % are w/w %.

Specific embodiments of the present invention are illustrated by way of the following examples. This invention is not confined to the specific limitations set forth in these examples, but rather to the scope of the appended claims. Unless otherwise stated, the percentages and ratios given below are by weight.

EXAMPLES

Example 1

| Ingredients | Unit Wt (mg) | % (w/w) | Batch Wt (g) |
|---|---|---|---|
| Simethicone** | 135 | 33.75 | 337.5 |
| Magnesium aluminometasilicate (NEUSILIN, US-2 from Fuji Chemical Ltd.) | 77 | 19.25 | 192.5 |
| Silicified microcrystalline cellulose (PROSOLV HD-90, from PenWest Co.) | 150 | 37.5 | 375.0 |
| Loperamide, USP | 2 | 0.5 | 5 |
| Sodium starch glycolate, NF | 32 | 8 | 80 |
| Stearic acid, NF | 4 | 1 | 10 |
| TOTAL | | | 1000 |

**Note:
10% overage added

In a 4 quart Hobart mixer, the magnesium aluminometasilicate and one-half of the batch quantity of the silicified microcrystalline cellulose were combined with the simethicone by initially sandwiching the simethicone between the magnesium aluminometasilicate (bottom) and the silicified microcrystalline cellulose (top) and mixed at speed setting "1" for about 5 minutes.

The loperamide was screened using a No. 40 mesh screen. After screening, the loperamine, sodium starch glycolate and remaining silicified microcrystalline cellulose were added to Hobart mixer and mixed at speed setting "1" for about 5 minutes.

The stearic acid was screened using a No. 30 mesh screen. After screening, the stearic acid was added to the Hobart mixer and mixed for about five minutes to form a free-flowing compressible powder.

The powder was then compressed into individual units, e.g., tablets, on a Manesty Beta Press with caplet shape standard concave tooling (diameter=6.092 mm, length=19.995 mm) through pre-compression at 5 kN followed by main compression. The target weight per unit was 400 mg. Each unit was measure for total weight, thickness (mm) and hardness (Kp) at various compression forces. Such data is presented below.

| Main Compression Force (kN) | Weight of 10 Units (g) | Average Thickness (mm) | Average Hardness (kp/cm²) |
|---|---|---|---|
| 5 | 4.037 | 5.135 | 5.75 |
| 10 | 3.990 | 4.943 | 6.64 |
| 12.5 | 3.947 | 4.814 | 7.5 |
| 15 | 3.906* | 4.743 | 5.88 |
| 20 | 3.912* | 4.687 | 5.95 |

*some picking upon compression.

Example 2

Simethicone (120 mg) Loperamide (2 mg) Caplets

| Ingredients | Unit Wt (mg) | % (w/w) | Batch Wt (g) |
|---|---|---|---|
| Simethicone | 135 | 33.75 | 33.75 |
| Magnesium aluminometasilicate-aluminometasilicate (NEUSILIN, US-2 from Fuji Chemical Ltd.) | 85 | 21.25 | 21.25 |
| Silicified microcrystalline cellulose (PROSOLV HD-90, from PenWest Co.) | 150 | 37.5 | 37.5 |
| Loperamide, USP | 2 | 0.5 | 0.5 |
| Sodium starch glycolate, NF | 26 | 6.5 | 6.5 |
| Stearic acid, NF | 2 | 0.5 | 0.5 |
| TOTAL | | | 100 |

In a glass mortar and pestle, the simethicone was levigated into the magnesium aluminometasilicate. The silicified microcrystalline cellulose was added to the dry simethicone/magnesium aluminometasilicate mixture and mixed thoroughly. The loperamide and sodium starch glycolate were added while mixing until uniform. The stearic acid was added and mixing was continued for about five minutes.

The powder was then compressed into individual units, e.g., tablets, on a Manesty Beta Press with caplet shape standard concave tooling (diameter=6.092 mm, length=19.995 mm) through pre-compression at 5 kN followed by main compression. Each unit was measured for total weight, thickness (mm) and hardness (kp) at various compression forces. Such data is presented below.

| Main Compression Force (kN) | Average Weight of Three Units (mg) | Average Thickness of Three Units (mm) | Average Hardness of Three Units (kp/cm²) |
|---|---|---|---|
| 3.5 | 421 | 5.602 | 10.16 |
| 5 | 424 | 5.29 | 9.62 |
| 7 | 410 | 4.601 | 5.71 |
| 10 | 418.3 | 5.129 | 7.68 |
| 18 | 402.7 | 4.89 | 5.37 |

Example 3

Simethicone (120 mg) Loperamide (2 mg) Caplets

| Ingredients | Unit Wt (mg) | % (w/w) | Batch Wt (g) |
|---|---|---|---|
| Simethicone | 135 | 31.034 | 62.1 |
| Magnesium aluminometasilicate (NEUSILIN, US-2 from Fuji Chemical Ltd) | 105 | 24.138 | 48.3 |
| Silicified microcrystalline cellulose (PROSOLV HD-90, from PenWest Co.) | 170 | 39.08 | 78.2 |
| Loperamide, USP | 2 | 0.4598 | 0.9 |
| Sodium starch glycolate, NF | 20 | 4.5977 | 9.2 |
| Stearic acid, NF | 3 | 0.6897 | 1.4 |
| TOTAL | | | 200 |

In a 4 quart Hobart mixer, the magnesium aluminometasilicate and one-half of the batch quantity of the silicified microcrystalline cellulose were combined with the simethicone by initially sandwiching the simethicone between the magnesium aluminometasilicate (bottom) and the silicified microcrystalline cellulose (top) and mixed at speed setting No. 1 for about 5 minutes.

The loperamide was screened using a No. 40 mesh screen. After screening, loperamide, sodium starch glycolate and remaining silicified microcrystalline cellulose were added to Hobart mixer and mixed at speed setting "1" for about 5 minutes.

The stearic acid was screened using a No. 30 mesh screen. After screening, the stearic acid was added to the Hobart mixer and mixed for about five minutes to form a free-flowing compressible powder.

The powder was then compressed into individual units, e.g., tablets, on a Manesty Beta Press with caplet shape standard concave tooling (diameter=6.092 mm, length=19.995 mm) through pre-compression at 3 kN followed by main compression. Each unit was measure for total weight, thickness (mm) and hardness (kp) at various compression forces. Such data is presented below.

| Main Compression Force (kN) | Average Weight of Five Units (mg) | Average Thickness of Five Units (mm) | Average Hardness of Five Units (kp/cm²) |
|---|---|---|---|
| 1 | 405 | 5.994 | 11.50 |
| 3.4 | 404.4 | 5.7522 | 15.24 |
| 5.0 | 371.6 | 5.129 | 15.87 |
| 6.0 | 390.2 | 5.145 | 17.23 |
| 7.5 | 394 | 5.164 | 15.26 |
| 10 | 390.6 | 4.874 | 13.13 |
| 13 | 386.4 | 4.763 | 10.30 |
| 20 | 397.8 | 4.795 | 8.18 |

While the target weight per unit was 435 mg, with tooling (604×224×052 BB caplet), i.e., volume of die at maximum, only about 400 mg weight was possible.

Example 4

A disintegration test comparing a unit from Example 1, (pre-compression 5 KN and main compression 5 kN) and a unit from Example 3 (pre-compression 3 kN and main compression 5 kN) in water was carried out. The results showed that the Example 1 unit disintegrated in less than about 2 minutes after the unit was placed in water, while the Example 3 unit remained intact and was floating in the water after about 2 and one-half minutes.

Example 5

Simethicone (120 mg) Loperamide (2 mg) Caplets

| Ingredients | Unit Wt (mg) | % (w/w) | Batch Wt (g) |
|---|---|---|---|
| Simethicone* | 135 | 33.75 | 67.5 |
| Magnesium aluminometasilicate (NEUSILIN, US-2 from Fuji Chemical Ltd.) | 90 | 22.5 | 45 |
| Silicified microcrystalline cellulose (PROSOLV HD-90, from PenWest Co.) | 150 | 37.5 | 75 |
| Loperamide, USP | 2 | 0.5 | 1 |
| Sodium starch glycolate, NF | 20 | 5 | 10 |
| Stearic acid, NF | 3 | 0.75 | 10 |
| TOTAL | | | 200 |

*Note:
10% overage added

In a 4 quart Hobart mixer bowl, simethicone was slowly added to about one-half of the batch quantity of the magnesium aluminometasilicate and mixed with a spatula for about 5 minutes.

The remaining magnesium aluminometasilicate was added to the mixture and mixing continued until the uniform, scraping the sides of the bowl.

The loperamide was screened using a No. 40 mesh screen. After screening, loperamide, sodium starch glycolate and the silicified microcrystalline cellulose were added. The resulting mixture was mixed at speed setting "1" for about five minutes.

The stearic acid was screened using a No. 30 mesh screen. After screening, the stearic acid was added and mixed for about five minutes to form a free-flowing compressible powder.

The powder was then compressed into individual units, e.g., tablets, on a Manesty Beta Press with caplet shape standard concave tooling (diameter=6.092 mm, length=19.995 mm) through pre-compression at 3 kN followed by main compression. Target weight was 400 mg per unit. Each unit was measure for total weight, thickness (mm) and hardness (kp) at various compression forces. Such data is presented below.

| Main Compression Force (kN) | Average Weight of Five Units (mg) | Average Thickness of Five Units (mm) | Average Hardness of Five Units (kp/cm$^2$) |
|---|---|---|---|
| 1 | 397.4 | 5.920 | 6.60 |
| 3.0 | 396.6 | 5.572 | 9.66 |
| 5.0 | 396.6 | 5.263 | 9.67 |
| 6.0 | 399.6 | 5.156 | 9.30 |
| 7.0 | 395.6 | 5.018 | 8.37 |
| 90 | 396.2 | 4.974 | 8.45 |
| 12.5 | 389.4 | 4.806 | 7.24 |
| 20.0 | 372.4 | 4.655 | <4.94 |

Example 6

Simethicone (120 mg) Loperamide (2 mg) Caplets

| Ingredients | Unit Wt (mg) | % (w/w) | Batch Wt (g) |
|---|---|---|---|
| Simethicone | 135 | 33.75 | 67.5 |
| Magnesium aluminometasilicate (NEUSILIN, US-2 from Fuji Chemical Ltd) | 100 | 25 | 50 |
| Silicified microcrystalline cellulose (PROSOLV HD-90, from PenWest Co.) | 140 | 35 | 70 |
| Loperamide, USP | 2 | 0.5 | 1 |
| Sodium starch glycolate, NF | 20 | 5 | 10 |
| Stearic acid, NF | 3 | 0.75 | 10 |
| TOTAL | | | 200 |

In a 4 quart Hobart mixer bowl, simethicone was slowly added to about one-half of the batch quantity of the magnesium aluminometasilicate and mixed with a spatula for about 5 minutes.

The remaining magnesium aluminometasilicate was added to the mixture and mixing continued until the uniform, scraping the sides of the bowl.

The loperamide was screened using a No. 40 mesh screen. After screening, loperamide, sodium starch glycolate and the silicified microcrystalline cellulose were added. The resulting mixture was mixed at speed setting "1" for about five minutes.

The stearic acid was screened using a No. 30 mesh screen. After screening, the stearic acid was added and mixed for about five minutes to form a free-flowing compressible powder.

The powder was then compressed into individual units, e.g., tablets, on a Manesty Beta Press with caplet shape standard concave tooling (diameter=6.092 mm, length=19.995 mm) through pre-compression at 3 kN followed by main compression. Target weight was 400 mg per unit. Each unit was measure for total weight, thickness (mm) and hardness (kp) at various compression forces. Such data is presented below.

| Main Compression Force (kN) | Weight of Five Units (mg) | Average Thickness of Five Units (mm) | Average Hardness of Five Units (kp/cm$^2$) |
|---|---|---|---|
| 1 | 395.6 | 5.773 | 6.94 |
| 2.0 | 398.2 | 5.672 | 8.57 |
| 3.0 | 400 | 5.263 | 10.23 |
| 4.0 | 395.8 | 5.296 | 7.81 |
| 5.0 | 390.8 | 5.1128 | 8.48 |
| 10 | 397.6 | 4.975 | <7.26 |
| 20 | 374.8 | 4.671 | 7.10 |

Example 7

Simethicone (120 mg) Loperamide (2 mg) Caplets

| Ingredients | Unit Wt (mg) | % (w/w) | Batch Wt (g) |
|---|---|---|---|
| Simethicone | 135 | 33.75 | 67.5 |
| Magnesium aluminometasilicate (NEUSILIN, US-2 from Fuji Chemical Ltd) | 110 | 27.5 | 55 |
| Silicified microcrystalline cellulose (PROSOLV HD-90, from PenWest Co.) | 125 | 31.25 | 62.5 |
| Loperamide, USP | 2 | 0.5 | 1 |
| Sodium starch glycolate, NF | 25 | 6.25 | 12.5 |
| Stearic acid, NF | 3 | 0.75 | 1.5 |
| TOTAL | | | 200 |

In a 4 quart Hobart mixer bowl, simethicone was slowly added to about one-half of the batch quantity of the magnesium aluminometasilicate and mixed with a spatula for about 5 minutes.

The remaining magnesium aluminometasilicate was added to the mixture and mixing continued until the uniform, scraping the sides of the bowl.

The loperamide was screened using a No. 40 mesh screen. After screening, the loperamine, sodium starch glycolate and the silicified microcrystalline cellulose were added. The resulting mixture was mixed at speed setting "1" for about five minutes.

The stearic acid was screened using a No. 30 mesh screen. After screening, the stearic acid was added and mixed for about five minutes to form a free-flowing compressible powder.

The powder was then compressed into individual units, e.g., tablets, on a Manesty Beta Press with caplet shape standard concave tooling (diameter=6.092 mm, length=19.995 mm) through pre-compression at 3 kN followed by main compression. Each unit was measure for total weight, thickness (mm) and hardness (kp) at various compression forces. Such data is presented below.

| Main Compression Force (kN) | Weight of Five Units (mg) | Average Thickness of Five Units (mm) | Average Hardness of Five Units (kp/cm$^2$) |
|---|---|---|---|
| 1 | 399 | 5.935 | 7.47 |
| 2 | 398.8 | 5.898 | 7.68 |
| 3.0 | 404.2 | 5.709 | 8.74 |
| 4.0 | 408 | 5.438 | 9.60 |
| 5.0 | 408.8 | 5.344 | 9.46 |
| 10.0 | 408.6 | 5.090 | 5.80 |
| 15.0 | 405.8 | 4.944 | <4.45 |
| 20.0 | 400.8 | 4.8716 | <4.04 |

Example 8

Simethicone (120 mg) Loperamide (2 mg) Caplets

| Ingredients | Unit Wt (mg) | % (w/w) | Batch Wt (g) |
|---|---|---|---|
| Simethicone** | 135 | 35.065 | 140.3 |
| Magnesium aluminometasilicate (NEUSILIN, US-2 from Fuji Chemical Ltd) | 90 | 23.377 | 93.5 |
| Silicified microcrystalline cellulose (PROSOLV HD-90 from Pen West Co.) | 146 | 37.922 | 151.7 |
| Loperamide, USP | 2 | 0.520 | 2.1 |
| Sodium starch glycolate, NF | 10 | 2.597 | 10.4 |
| Stearic acid, NF | 2 | 0.520 | 2.1 |
| TOTAL | | | 400 |

**Note: 10% overage added

In a 4 quart Hobart mixer bowl, simethicone was slowly added to about one-half of the batch quantity of the magnesium aluminometasilicate and mixed with a spatula for about 5 minutes.

The remaining magnesium aluminometasilicate was added to the mixture and mixing continued until the uniform, scraping the sides of the bowl.

The loperamide was screened using a No. 40 mesh screen. After screening, the loperamine, sodium starch glycolate, NF and the silicified microcrystalline cellulose were added. The resulting mixture was mixed at speed setting "1" for about five minutes.

The stearic acid was screened using a No. 30 mesh screen. After screening, the stearic acid was added and mixed for about five minutes to form a free-flowing compressible powder.

The powder was then compressed into individual units, e.g., tablets, on a Manesty Beta Press with caplet shape standard concave tooling (diameter=6.092 mm, length=19.995 mm) through pre-compression at 3 kN followed by main compression (* these units were not pre-compressed). Target weight was 385 mg per unit. Each unit was measure for total weight, thickness (mm) and hardness (kp) at various compression forces. Such data is presented below.

| Main Compression Force (kN) | Average Weight of Five Units (mg) | Average Thickness of Five Units (mm) | Average Hardness of Five Units (kp/cm$^2$) |
|---|---|---|---|
| 1 | 382.8 | 5.460 | 9.56 |
| 2 | 383.4 | 5.395 | 9.31 |
| 3.0 | 382 | 5.356 | 7.60 |
| 4.0 | 379.8 | 5.123 | 8.78 |
| 5.0 | 382.8 | 4.993 | <6.58 |
| 10.0 | 383.6 | 4.841 | <4.07 |
| 1.5* | 384.8 | 5.439 | 7.12 |
| 3.0* | 382.4 | 5.306 | 7.61 |

Example 9

Simethicone (120 mg)/Acetaminophen (250 mg) Caplets

| Ingredients | Unit Wt (mg) |
| --- | --- |
| Simethicone** | 135 |
| Magnesium aluminometasilicate (NEUSILIN, US-2 from Fuji Chemical Ltd) | 90 |
| Silicified microcrystalline cellulose (PROSOLV HD-90 from Pen West Co.) | 150 |
| Acetaminophen, USP | 250 |
| Sodium starch glycolate, NF | 20 |
| Stearic acid, NF | 5 |
| TOTAL | 650 |

**Note: 10% overage added

In a 4 quart Hobart mixer bowl, simethicone is slowly added to about one-half of the batch quantity of the magnesium aluminometasilicate with mixing using a spatula for about 5 minutes.

The remaining magnesium aluminometasilicate is added to the mixture and mixing continued until the uniform, scraping the sides of the bowl.

The acetaminophen is screened using a No. 40 mesh screen. After screening, the acetaminophen, sodium starch glycolate, NF and the silicified microcrystalline cellulose are added. The resulting mixture is mixed at speed setting "1" for about five minutes.

The stearic acid is screened using a No. 30 mesh screen. After screening, the stearic acid is added and mixed for about five minutes to form a free-flowing compressible powder.

Example 10

Simethicone (120 mg)/Ibuprofen (200 mg) Caplets

| Ingredients | Unit Wt (mg) |
| --- | --- |
| Simethicone** | 135 |
| Magnesium aluminometasilicate (NEUSILIN, US-2 from Fuji Chemical Ltd) | 90 |
| Silicified microcrystalline cellulose (PROSOLV HD-90 from Pen West Co.) | 150 |
| Ibuprofen, USP | 200 |
| Sodium starch glycolate, NF | 20 |
| Stearic acid, NF | 5 |
| TOTAL | 600 |

**Note: 10% overage added

In a 4 quart Hobart mixer bowl, simethicone is slowly added to about one-half of the batch quantity of the magnesium aluminometasilicate with mixing using a spatula for about 5 minutes.

The remaining magnesium aluminometasilicate is added to the mixture and mixing continued until the uniform, scraping the sides of the bowl.

The ibuprofen is screened using a No. 40 mesh screen. After screening, the ibuprofen, sodium starch glycolate, NF and the silicified microcrystalline cellulose are added. The resulting mixture is mixed at speed setting "1" for about five minutes.

The stearic acid is screened using a No. 30 mesh screen. After screening, the stearic acid is added and mixed for about five minutes to form a free-flowing compressible powder.

Example 11

Simethicone (120 mg)/Mesalamine (400 mg) Caplets

| Ingredients | Unit Wt (mg) |
| --- | --- |
| Simethicone** | 135 |
| Magnesium aluminometasilicate (NEUSILIN, US-2 from Fuji Chemical Ltd) | 110 |
| Silicified microcrystalline cellulose (PROSOLV HD-90 from Pen West Co.) | 125 |
| Mesalamine (5-aminosalicylic acid, 5-ASA) | 2 |
| Stearic acid, NF | 10 |
| TOTAL | 781 |

**Note: 10% overage added

In a 4 quart Hobart mixer bowl, simethicone was slowly added to about one-half of the batch quantity of the magnesium aluminometasilicate and mixed with a spatula for about 5 minutes.

The remaining magnesium aluminometasilicate was added to the mixture and mixing continued until the uniform, scraping the sides of the bowl.

The mesalamine is screened using a No. 40 mesh screen. After screening, the mesalamine and the silicified microcrystalline cellulose are added. The resulting mixture was mixed at speed setting "1" for about five minutes.

The stearic acid is screened using a No. 30 mesh screen. After screening, the stearic acid is added and mixed for about five minutes to form a free-flowing compressible powder.

What is claimed is:

1. A composition for forming a compressed solid dosage form comprising a free-flowing compressible admixture of simethicone and an adsorbent comprising silicified microcrystalline cellulose and magnesium aluminometasilicate, wherein the weight ratio of simethicone to adsorbent is at least about 1:1.75, and wherein the composition has at least 30 wt % simethicone.

2. A composition of claim 1, further comprising at least one additional active agent.

3. A composition of claim 2, wherein the active agent is selected from the group consisting of a bisacodyl, a famotidine, a prucalopride, a diphenoxylate, a loperamide, a lactase, a mesalamine, a bismuth, and pharmaceutically acceptable salts and mixtures thereof.

4. A composition of claim 3, wherein the active agent is loperamide, or pharmaceutically acceptable salts thereof.

5. A composition of claim 1, having from 31 wt % to 35 wt % simethicone.

6. A composition of claim 1, having from about 19 wt % to about 27 wt % silicified microcrystalline cellulose and having from about 31 wt % to about 39 wt % magnesium aluminometasilicate.

7. A composition of claim 6, having from about 23 wt % to about 27 wt % silicified microcrystalline cellulose and from about 33 wt % to about 37 wt % magnesium aluminometasilicate.

8. A composition of claim 1, wherein the composition is compressed into a tablet having a hardness value of at least 2 kp/cm$^2$.

9. A composition of claim 8, wherein the composition is compressed into a tablet having a hardness value of from about 5 to about 10 kp/cm$^2$.

10. A solid oral dosage form comprising a compressed admixture of simethicone, silicified microcrystalline cellulose, and magnesium aluminometasilicate, wherein the simethicone is adsorbed on the silicified microcrystalline cellulose and magnesium aluminometasilicate, wherein the weight ratio of simethicone to the silicified microcrystalline cellulose and magnesium aluminometasilicate adsorbent is at least about 1:1.75, and wherein the composition has at least 30 wt % simethicone.

11. A solid oral dosage form of claim 10, further comprising at least one additional active agent.

12. A solid oral dosage form of claim 11, wherein the active agent is selected from the group consisting of a bisacodyl, a famotidine, a prucalopride, a diphenoxylate, a loperamide, a lactase, a mesalamine, a bismuth, and pharmaceutically acceptable salts and mixtures thereof.

13. A solid oral dosage form of claim 12, wherein the active agent is loperamide, or pharmaceutically acceptable salts thereof.

14. A solid oral dosage form of claim 10, having from 31 wt % to 35 wt % simethicone.

15. A solid oral dosage form of claim 10, having from about 19 wt % to about 27 wt % silicified microcrystalline cellulose and having from about 31 wt % to about 39 wt % magnesium aluminometasilicate.

16. A solid oral dosage form of claim 15, having from about 23 wt % to about 27 wt % silicified microcrystalline cellulose and from about 33 wt % to about 37 wt % magnesium aluminometasilicate.

17. A solid oral dosage form of claim 10, wherein the composition is compressed into a tablet having a hardness value of at least 2 kp/cm$^2$.

18. A solid oral dosage form of claim 10, wherein the composition is compressed into a tablet having a hardness value of from about 5 to about 10 kp/cm$^2$.

19. A composition of claim 3, wherein the active agent is bisacodyl, or pharmaceutically acceptable salts thereof.

20. A composition of claim 2, wherein the active agent is selected from the group consisting of acetaminophen, ibuprofen, naproxen, ketoprofen, cyclobenzaprine, meloxicam, rofecoxib, celecoxib, and pharmaceutically acceptable salts and mixtures thereof.

\* \* \* \* \*